United States Patent
Caruso et al.

(10) Patent No.: US 8,034,335 B2
(45) Date of Patent: Oct. 11, 2011

(54) HIGH-TITER RETROVIRAL PACKAGING CELLS

(75) Inventors: Manuel Caruso, Québec (CA); Karim Ghani, Québec (CA)

(73) Assignee: Universite Laval, Quebec, Quebec (CA)

( * ) Notice: Subject to any disclaimer, the term of this patent is extended or adjusted under 35 U.S.C. 154(b) by 281 days.

(21) Appl. No.: 12/298,169

(22) PCT Filed: Apr. 26, 2007

(86) PCT No.: PCT/CA2007/000708
§ 371 (c)(1),
(2), (4) Date: Oct. 23, 2008

(87) PCT Pub. No.: WO2007/124573
PCT Pub. Date: Nov. 8, 2007

(65) Prior Publication Data
US 2009/0098648 A1     Apr. 16, 2009

Related U.S. Application Data

(60) Provisional application No. 60/745,911, filed on Apr. 28, 2006.

(51) Int. Cl.
C12N 15/867 (2006.01)
C12N 15/09 (2006.01)
C12N 15/11 (2006.01)
C12N 15/33 (2006.01)
C12N 5/00 (2006.01)

(52) U.S. Cl. ...... 424/93.7; 435/325; 435/455; 536/23.1; 536/23.72

(58) Field of Classification Search .................. None
See application file for complete search history.

(56) References Cited

U.S. PATENT DOCUMENTS

| 5,834,256 A | 11/1998 | Finer et al. |
| 5,910,434 A | 6/1999 | Rigg et al. |
| 6,210,922 B1 | 4/2001 | Côté et al. |
| 7,015,035 B2 * | 3/2006 | Ward et al. ............... 435/325 |
| 2006/0270042 A1 * | 11/2006 | Caruso et al. ............ 435/456 |

FOREIGN PATENT DOCUMENTS

WO    2005/047497    5/2005

OTHER PUBLICATIONS

Ghani K. et al., 2006, "Development of Packaging Cell Lines for the Large-Scale Production of High-Titer Clinical Grade Recombinant Retroviruses.", Molecular Therapy, vol. 13, pp. S317-S318.

(Continued)

Primary Examiner — Maria Marvich
(74) Attorney, Agent, or Firm — Norton Rose LLP (57) ABSTRACT

The present invention relates to non-replicative recombinant retrovirus packaging cells able to grow in suspension in a serum-free medium. In particular, the present invention relates to a human embryonic 293SF-based cell line stably expressing gag and pol gene products from the murine Moloney leukemia virus (MLV) and either the feline RD114 env gene, the gibbon ape leukemia virus (GLV) env gene, or the amphotropic 4070Aenv gene. This particular combination allows the production of high titer of non-replicative retrovirus pseudotyped and prevents the recombination of plasmids. The recombinant retroviruses produced from these cells are safer and easier to produce for clinical use in gene therapy.

1 Claim, 5 Drawing Sheets

PACKAGING VECTOR

A)

ENVELOPE VECTOR

B)

TRANSFER VECTOR

C)

D)

E)

OTHER PUBLICATIONS

Ghani K. et al., 2007, "Generation of a high-titer packaging cell line for the production of retroviral vectors in suspension and serum-free media.", Gene Therapy, vol. 14, No. 24, pp. 1705-1711.

Ghani K. et al., 2009, "Efficient Human Hematopoietic Cell Transduction Using RD114-and GALV-Pseudotyped Retroviral Vectors Produced in Suspension and Serum-Free Media.", Human Gene Therapy, vol. 20, No. 9, pp. 966-974.

Chomez, P., et al. "An Overview of the MAGE Gene Family with the Identification of All Human Members of the Family", Cancer Research, 2001, vol. 61, pp. 5544-5551. ISSN 008-5472.

Abnova Corporation Catalogue (Under Copyright, last updated, Jul. 1, 2005; online). MAGEA9 product search [retrieved on Jan. 25, 2007]. Retrieved from the Internet: <URL:http://www.abnova.com.tw/product_search/PS_search_All.asp?GS_searchbox=MAGEA9>.

Oehlrich, N., et al. "Generation of RAGE-1 and MAGE-9 Peptide-Specific Cytotoxic T-Lymphocyte Lines for Transfer in Patients with Renal Cell Carcinoma", Int. J. Cancer, Nov. 1, 2005, vol. 117, pp. 256-264. ISSN 0020-7136.

Miller A., et al. "Construction and Properties of Retrovirus Packaging Cells Based on Gibbon Ape Leukemia Virus", Journal of Virology, May 1991, vol. 65, No. 5, pp. 2220-2224.

Ward et al. "A Stable Murine-Based RD114 Retroviral Packaging Line Efficiently Transduces Human Hematopoietic Cells", Molecular Therapy, Nov. 2003, vol. 8, No. 5, pp. 804-812.

Ghani K et al. "Retroviral Vector Production Using Suspension-Adapted 293GPG Cells in a 3L Acoustic Filter-Based Perfusion Bioreactor" Biotechnol Bioeng 2006; 95: 653-660.

* cited by examiner

HIGH-TITER RETROVIRAL PACKAGING CELLS

CROSS-REFERENCE TO RELATED APPLICATION

This application claims priority from U.S. provisional application 60/745,911 filed on Apr. 28, 2006 incorporated herein by reference.

FIELD OF THE INVENTION

The present invention relates to the production of cell lines for the packaging of non-replicative retrovirus particles. The present invention also relates to packaging cells capable of growing in a serum-free medium and in suspension to minimize biohazard risks and increase the virus titer.

BACKGROUND OF THE INVENTION

The life cycle of retroviruses involves an obligatory stage in which the virus genetic material is inserted into the genome of a host cell by transposition-like events. This step is essential because the inserted viral nucleic acid, the provirus, is replicated through the host cell machinery.

Because retroviruses have genomes of diploid single-stranded RNA (ssRNA), those must be replicated through a double-stranded DNA intermediate prior to their insertion. The initial conversion of the viral RNA molecule into a double-stranded DNA (dsDNA) molecule is performed by a reverse-transcriptase. The dsDNA is then led to the nucleus, where one or more copies are integrated to the genome by an integrase to further be replicated by the host cellular machinery. The reverse transcriptase and the integrase required for the conversion of ssRNA into dsDNA and for the integration into the host genome are carried within the viral particle during host cell infection. The proviral DNA is finally transcribed using the host machinery into multiple RNA copies. These RNA molecules will further be translated into virus peptides or integrated into virus particles which will be released from the cell into the extracellular milieu.

Retrovirus RNA molecules usually comprise 6 typical regions leading to the expression of multiple proteins by processing reactions These typical retrovirus region include the gag, pol and env gene sequences associated to a psi (ψ) signal and flanked by 5' and 3' long terminal repeats (LTR) sequences. The gag gene leads to the expression of the protein components of the nucleoprotein core of the virus, while the pol gene products are involved in the synthesis of nucleic acid and recombination. The env gene codes for the envelope components of the retrovirus particle. 5' and 3' LTR sequences of those genes ensure the correct transcription of the virus RNA into DNA and subsequent integration of the virus genome into the chromosomal DNA of the cell. Finally, the psi signal refers to the retroviral packaging signal that controls the efficient packaging of the RNA into the virus particle, and thus to gene transfer.

Because of their ability to form proviruses, retroviruses appeared as adequate tools to modify the genome of particular cells for uses such as gene therapy. Gene therapy using retroviral vectors is generally performed by adding an exogenous nucleic acid sequence to the retroviral RNA vector, packaging this vector into a virus particle and infecting a target host cell. The target cell will then incorporate the exogenous gene as being a part of a provirus.

For safety reasons, retroviral vectors must be replication incompetent, since the target cell would suffer from a retroviral infection. The use of vector systems now allows the production of recombinant retroviruses that are unable to replicate by themselves. Those systems make use of virus that comprise the exogenous gene of interest, flanked only by the minimal sequences required for retrotranscription into DNA, insertion into the host cell genome and proper expression of this gene. The RNA molecule carried by the non-replicative retroviral particle is devoid of gag, pol and env genes and therefore, the target cell does not produce the nucleoprotein core nor the envelope essential to the replication of the virus.

To infect target cells, encapsidation of the exogenous RNA molecule however remains a necessary step. Therefore, a complementation system must be provided in packaging cells. The virus assembly is performed in packaging cells infected with helper virus or now more generally with viruses transiently or stably transfected with constructs comprising psi-negative gag, pol and env genes.

Transfection of a psi-positive construct comprising the exogenous gene into such infected or transfected packaging cells leads to the encapsidation of the RNA molecule into a virus. Next, the packaging cells release the retroviral vector particles, or virus, into the supernatant. As gag-pol and env genes are not carried by the virus particle, those genes cannot be transferred from the packaging cells to the target cells.

Packaging cells are frequently designed to express retroviral vectors that are derived from the Moloney murine leukemia virus (MLV). In fact, MLV-derived vectors are the most commonly used vectors in clinical trials for gene therapy. Although these replication-defective recombinant retroviruses can be produced by transient cotransfection of an expression vector comprising the exogenous gene and packaging plasmids coding for gag-pol and env viral proteins, the absence of toxicity of MLV proteins has made possible the generation of stable retrovirus-producer cell lines which are convenient for use in large-scale vector production. To improve the infectious properties of recombinant retroviruses, env gene products of more infectious viruses can be used. This process, known as pseudotyping, is commonly used to modify the virus tropism to make it more infectious and/or more specific to a specific cell type. For example, retroviral vectors pseudotyped with the feline leukemia RD114 env glycoprotein have been shown to be very promising for gene therapy, particularly since they show resistance to complement inactivation and are efficient to transfer genes into human lymphocytes and hematopoietic stem cells.

One major safety concerned with stable packaging cell lines is to ensure that expression vectors generated from these packaging cells are not contaminated with replication-competent retroviruses (RCRs). RCRs result from the recombination between the expression vector and the packaging plasmids. It has also been shown that non human primates can develop lymphomas after being grafted with genetically modified hematopoietic stem cells contaminated with RCR. To prevent such deleterious recombinations, the latest generations of packaging cells use an expression vector and a packaging plasmid that have reduced overlapping homologies in retroviral sequences, reducing the risk of generating replication competent viruses.

Although the latest generations of packaging cell lines are effective in protecting from RCR contamination, the scale up for clinical uses is limitative because of the adherence of those cells. Indeed, since the growing environment of cells is limited to the surface of a recipient, the production of large volumes of retroviruses is cumbersome and can be quite expensive. In addition, most of the cells actually used for packaging require the use of animal serum for their growth. This represents another drawback for the existing packaging cell lines because of the biohazard contamination risks. Finally, murine cells used in the production of MLV particles can produce a characteristic α-galactosyl epitope at the surface of the virus. This epitope can be recognized by the immune system of the host organism, causing an antibody-mediated inactivation of the recombinant retrovirus particles.

Recently, a human embryonic kidney (HEK) cell line, the 293SF cell line, has been developed (U.S. Pat. No. 6,210,922) and is a good candidate to bypass the above-mentioned drawbacks generally associated with packaging cells. First, these cells are human cells and therefore do not produce the carbohydrate structure α-galactosyl epitope found at the surface of the virus produced from murine cells. In addition, the genomic DNA from these cells does not hybridized with MLV specific probes at low or high stringency, therefore precluding the generation of RCR by recombination with endogenous retrovirus, as found with murine packaging cell lines. Stable packaging cells have already been derived from HEK 293 cells and it seems that they have the property to produce recombinant retroviruses with relatively high titers. Finally, 293SF cells grown in suspension in a serum-free media are already available and are used for the large scale production of proteins and adenoviral vectors.

Considering the state of the prior art, it would be desirable to be provided with a packaging cell line that grows in suspension with serum-free medium and is capable of expressing high titers of recombinant retrovirus particles precluding the generation of RCR.

SUMMARY OF THE INVENTION

One advantage of the present invention is to provide a retrovirus packaging cell line, preferably a human embryonic kidney (HEK) 293-based cell line, for the production of a non-replicative retrovirus particle. Particularly, this cell line is capable of growing in suspension, in a serum-free medium or simultaneously both in suspension and serum free conditions. The nucleic acid component of the non-replicative retrovirus particle comprises a nucleic acid sequence of interest and is capable of being incorporated into the genome of a target host cell.

Another advantage of the present invention is to provide a retrovirus packaging cell line for the production of a non-replicative retrovirus particle, said cell line stably expressing gag gene, pol gene and env gene, wherein said gag gene and pol gene originate from murine Moloney leukemia virus, and wherein said env gene originates from a gene selected from the group consisting of feline RD114 env gene, gibbon ape leukemia virus env gene, and amphotropic 4070A env gene.

Another advantage of the present invention is to provide a retrovirus packaging cell line for the production of non-replicative retrovirus particles, wherein said retrovirus packaging cell line is a 293SF cell line which produces moloney murine leukemia virus cores with RD114 virus cat envelope and bears the deposit name R030 (Accession number 310106-01, Jan. 31, 2006) at the International Depositary Authority of Canada, 1015 Arlington Street, Winnipeg. Manitoba. Canada, R3E 3R2.

Another advantage of the present invention is to provide a retrovirus packaging cell line for the production of non-replicative retrovirus particles, wherein said retrovirus packaging cell line is a 293SF cell line which produces moloney murine leukemia virus cores with Gibbon ape leukemia virus envelope and bears the deposit name GLV9 (Accession number 310106-02, Jan. 31, 2006) at the international Depositary Authority of Canada, 1015 Arlington Street, Winnipeg, Manitoba. Canada, R3E 3R2.

Another advantage of the present invention is to provide a retrovirus packaging cell line for the production of non-replicative retrovirus particles, wherein said retrovirus packaging cell line is 293SF cell line which produces moloney murine leukemia virus cores with MuLV amphotrope envelope and bears the deposit name A2 (Accession number 310106-04, Jan. 31, 2006) at the International Depositary Authority of Canada, 1015 Arlington Street. Winnipeg, Manitoba. Canada. R3E 3R2.

Another advantage of the present invention is to provide a method for producing non-replicative retrovirus particles comprising transfecting a mammalian cell with a gag gene, a pol gene and a env gene, wherein said gag gene and pol gene originate from murine Moloney leukemia virus, and wherein said env gene originates from any one of the group consisting of feline RD114 env gene, gibbon ape leukemia virus env gene, and amphotropic 4070A env gene, and maintaining said mammalian cell in culture conditions allowing the replication of said mammalian cell.

A further advantage of the present invention is to provide the use of a retrovirus-producing cell line for the manufacture of a composition comprising non-replicative retroviral particles for the treatment of diseases treatable with gene therapy.

A further advantage of the present invention is to provide a method of treatment of diseases treatable with gene therapy, the method comprising administering to a patient in need thereof a composition made in accordance with the present invention.

For the purpose of the present invention the following terms are defined below.

The term "gene product" as used herein is intended to mean a peptide, a protein or a RNA molecule encoding these peptides or proteins, resulting from the expression of a gene or any encoding nucleic acid. The term "gene" is intended to mean a DNA molecule that encodes a peptide or a protein, or that can be translated into a RNA molecule. The term "gene" further encompass any regulatory DNA sequence that does not encode for a peptide or a protein, or is not translated into RNA, but that can regulate the expression or the translation of another DNA sequence.

The terms "originating" and "originate" as used herein as descriptive of a gene are intended to describe the source of the gene, the species or organisms in which those genes are naturally present.

The terms "dissociating" and "dissociate" as used herein as descriptive of a gene and are intended to highlight the absence of a genetic element, domain or fragment, that is usually present found in association with said gene. In an embodiment, genes are dissociated from one another when they are not physically associated, e.g. when they are not present on the same nucleic acid molecule (trans configuration).

The term "polypeptide" as used herein is intended to mean any protein, peptide, polypeptide or the like that is native or not to the host cell line. A gene or nucleic acid encoding for the polypeptide may therefore originate from an animal, including human, a plant, a fungus, a bacterium or any other living species or organisms. In addition, the polypeptide can be synthesized from a synthetic gene or nucleic acid, synthesized exclusively by human hand, or naturally produced and further modified by human hand, wherein the polypeptide is different from what is naturally found in the host cell. A recombinant polypeptide may therefore originate from the host cell itself (homologous polypeptide) although having been genetically manipulated for production purposes.

The term "RCR" as used herein is intended to mean a replication-competent retrovirus (RCR). A replication-competent virus is a viral particle that has the capacity to replicate by itself in a host cell.

The term "non-replicative retrovirus particle" as used herein is intended to mean a retrovirus particle that does not possess the capacity to replicate by itself in a host cell, or a retrovirus particle that normally has the capacity to replicate by itself in a host cell but that has been modified in such a way that it had lost this capacity.

The term "IRES" as used herein is intended to mean internal ribosomal entry site.

The terms "transfecting" or "transfection" as used herein are intended to mean the transfer of at least one exogenous nucleic acid in an eukaryotic cell. The nucleic acid may be RNA, DNA or a combination of both. The exogenous nucleic acid refers to nucleic that is not found as a result of host cell division or host cell multiplication. This nucleic acid may be originating from a foreign organism or species or from the species from which the transfected cell originates.

The term "virus" as used herein is intended to mean the physical virus or retrovirus particle, irrespective of its ability of infecting a host cell or reproducing into the host cell.

The term "cell line" as used herein refers to cultured cells that can be passed (divided) more than once. The invention relates to cell lines that can be passed more than 2 times, up to 200 times, or preferably more than any integer between 2 and 200, each number not having been explicitly set forth in the interest of conciseness.

The expressions "stable expression" and "stably expressing" as used herein are intended to mean that the genetic material that is being stably expressed and/or is integrated permanently and stably in the genome of the host cell, and thus has the same expression potential over time as the native genetic material of the host cell.

The terms 293GP-A2 and "A2" are used herein interchangeably.

The terms 293GP-21C and "GP21C" are used herein interchangeably.

The terms 293GP-GLV9 and "GLV9" are used herein interchangeably.

The terms 293GP-RD30 and "RD30" are used herein interchangeably.

DETAILED DESCRIPTION OF PARTICULAR EMBODIMENTS

The present invention now will be described more fully hereinafter with reference to the accompanying drawings, in which preferred embodiments of the invention are shown. This invention, may, however, be embodied in many different forms and should not be construed as limited to the embodiments set forth herein. Rather, these embodiments are provided so that this disclosure will be thorough and complete, and will fully convey the scope of the invention to those skilled in the art.

In accordance with the present invention, there is provided a retrovirus packaging cell line, that can be a human embryonic kidney (HEK) 293-based cell line, for the production of a non-replicative retrovirus particle. The cell line of the present invention stably expresses the components, as for example gag, pol, and env gene products, required for the assembly of a non-replicative recombinant retrovirus particles. Moreover, the nucleic acid component of the recombinant retrovirus particles comprises a nucleic acid sequence of interest and is capable of being incorporated into the genome of a target host cell. The expression vector and packaging plasmids to be used in accordance with the present invention have low homologies with one another, thereby reducing the risks of generating replication competent viruses.

In a further embodiment of the present invention, 293-based cells are 293SF cells and preferably the 293SF cells having the deposit name RD30 (Accession number 310106-01, Jan. 31, 2006), GLV9 (Accession number 310106-02, Jan. 31, 2006), GP21C (Accession number 310106-03, Jan. 31, 2006), and A2 (Accession number 310106-04, Jan. 31, 2006) at the International Depositary Authority of Canada.

In one embodiment of the present invention, the packaging cell line is capable to grow in suspension or in a serum-free medium. The packaging cell line can also be grown both in serum-free medium and suspension simultaneously. Although serum-free medium and the capacity to grow in suspension are the preferred conditions of the present invention, for their capacity to optimize or maximize the yield of non-replicative retrovirus particle titer, the 293SF cells of the present invention can be cultured in an adherent manner with regular serum-containing medium to achieve particular purposes. Such purposes can be, for example, to facilitate transfection of cells or to select cell clones.

The type of packaging cells used to generate the retrovirus determines the tropism or host range for the virus. These cell lines have the essential retroviral genes -gag, pol and env integrated separately in its genome. Development of synthetic packaging lines is herein a major development that advances utility of retrovirus as a gene delivery vehicle. It ends use of replication competent or helper viruses.

In another embodiment of the present invention, the nucleic acid component of the non-replicative retrovirus particles is ribonucleic acid (RNA). This RNA molecule comprises a nucleic acid sequence of interest used for gene therapy. As the psi ($\psi$) factor commands the encapsidation of a RNA molecule into a retrovirus particle, in one embodiment of the present invention, a nucleic acid sequence of interest is associated with a psi factor.

In another embodiment of the present invention, the nucleic acid component of the non-replicative retrovirus particle encodes a gene, a promoter or a combination thereof. The gene of interest can code for an antibody, an antigen, an antisense RNA, a cytokine, a drug resistance factor, a hormone, a deficiency factor, a marker, a trans-dominant factor, an oncogene regulator, a receptor, a ribozyme, a suicide factor, a tumor suppressor, any other gene or multiple genes, or any combinations thereof for conferring a particular physiological reaction. For the purpose of the present invention, promoter sequences are preferably aimed to provide adequate regulation of the expression of genes under their control. Therefore, the nucleic acid sequence of interest of the present invention preferably comprises a gene located downstream a promoter sequence that controls its expression properly. Both gene and promoter sequences can be naturally occurring nucleic sequences cloned into the viral vector, naturally occurring sequences that have been genetically altered or synthetic sequences.

The components required for the assembly of said recombinant retrovirus particle are gag, pol and env gene products. Since the psi ($\psi$) factor commands the incorporation of a RNA molecule into a virus, it is an embodiment of the present invention to provide env, gag and pol gene products that are dissociated from psi ($\psi$) factor. The mRNA stably expressed by the packaging cell line can therefore be translated properly by the cell machinery while avoiding the possibility of being incorporated into the retrovirus particle. Since the gene products of these three genes are essential to the replicative capacity of retroviruses, the absence of the gag, pol and env genes within the nucleic acid sequence carried by the viruses of the present invention confers to the virus the important characteristic of being non-replicative.

In another embodiment of the present invention, the gag and pol gene products can be derived from a murine Moloney leukemia virus (MLV) and the env gene product is derived preferably from, but not limited to, either a feline leukemia RD114 env gene product, a GLV env gene product, or a 4070A env gene product. A MLV gag-pol expression plasmid containing a resistance selectable marker was chosen (Zeocin™ ($zeo^r$) or puromycin-N-acetyl transferase ($puro^r$) gene for example) linked to an internal ribosomal entry site (IRES) is preferably used to generate gag-pol expressing 293SF clones. The env expression plasmid is preferably constructed by cloning a feline leukemia RD114 env gene followed by a resistance selectable marker gene (such as $puro^r$) linked to an IRES, a gibbon ape leukemia (GLV) env gene followed by a resistance selectable marker gene (such as $puro^r$) linked to an IRES, or an amphotropic 4070A env gene followed by a resistance selectable marker gene (such as $puro^r$) linked to an IRES.

Use of MLV gag and pol and either RD114 env, GLV env or 4070A env genes are designed to ensure that the exogenous nucleic acid molecules cannot recombine with one another to form replicative-competent retroviruses. Since the expression vector of the present invention and the packaging plasmids have such low overlapping homologies, the generation of replication competent retroviruses is very unlikely.

In addition, the RD114 env gene is preferred since it confers to the virus a resistance to complement inactivation, as well as efficient gene transfer into human lymphocytes and hematopoietic stem cells. Although this combination of gag, pol and env gene is preferred, a skilled artisan could use any vector and plasmid sets capable of providing similar properties to the packaging cell line.

In a further embodiment of the present invention, there is provided a method for the treatment of diseases treatable with gene therapy, the method comprising administering to a patient in need thereof a composition made in accordance with the present invention.

In a further embodiment of the present invention, there is provided a vaccine for the prevention or the treatment of diseases preventable or treatable with a vaccine, the vaccine comprising a composition made in accordance with the present invention.

The HEK 293-based packaging cell line is used to produce high titer of non-replicative retroviral particles for use in gene therapy or vaccines. Gene therapy as intended herein consists in the modification of the genome of at least one cell of a patient or target organism. The modification of the genome comprises the addition of genetic material into a cell genetic pool by gene insertion either to correct a hereditary disease or to modify the characteristics of the cell via expression of the newly inserted gene. Therefore, gene therapy can be used in a healthy patient or target organism to genetically enhance a particular physical trait or physiological characteristic. However, the purpose of the present invention is preferably the prevention, treatment or cure of diseases via gene therapy or vaccines that include, but are not limited to, cancer, monogenic diseases, infectious diseases, vascular diseases and other diseases.

Other genetic diseases that can be treated according to the present invention include, but are not limited to, Chronic Granulomatous Disease, Duchenne Muscular Dystrophy, Retinobastoma, Cystic Fibrosis, Wilms Tumor, Neurofibromatosis Type 1, Testis Determining Factor, Choroideremia, Fragile X Syndrome, Familial Polyposis Coli, Kallmann Syndrome, Aniridia, Myotonic Dystrophy, Lowe Syndrome, Norrie Syndrome, Menkes Disease, X-Linked Agammaglobulinemia, Glycerol Kinase Deficiency, Adrenoleukodystrophy, Neurofibromatosis Type 2, Huntington Disease, Von Hippel-Lindau Disease, Spinocerebellar Ataxia 1, Lissencephaly, Wilson Disease, Tuberous Sclerosis, McLeod Syndrome, Polycystic Kidney Disease Type 1, Dentatorubral Pallidoluysian Atrophy, Fragile X "E", Achondroplasia, Wiskott Aldrich Syndrome, Early Onset Breast/Ovarian Cancer (BRCA1), Diastrophic Dysplasia, Aarskog-Scott Syndrome, Spinocerebellar Ataxia 3, Congenital Adrenal Hypoplasia, Emery-Dreifuss Muscular Dystrophy, Machado-Joseph Disease, Spinal Muscular Atrophy, Chondrodysplasia Punctata, Limb-Girdle Muscular Dystrophy, Ocular Albinism, Ataxia Telangiectasia, Alzheimer's Disease, (Chromosome 1 and/or 14), Hypophosphatemic Rickets, Hereditary Multiple Exostoses (EXT1 and/or EXT2), Bloom Syndrome, Early Onset Breast Cancer (BRCA2), Friedreich's Ataxia, Progressive Myoclonic Epilepsy, Treacher Collins Syndrome, Long QT Syndrome (Chromosome 11), Barth Syndrome, Simpson-Golabi-Behmel Syndrome, Werner's Syndrome, X-Linked Retinitis Pigmentosa (RP3), Polycystic Kidney Disease, Type 2, Basal Cell Nevus Syndrome, X-linked Myotubular Myopathy, Anhidrotic Ectodermal Dysplasia, Hemochromatosis, Chediak-Higashi Syndrome, Fanconi Anemia A, Hermansky-Pudlak Syndrome, Spinocerebellar Ataxia 2, CADASIL (Hereditary Stroke), Rieger Syndrome, Maturity-Onset Diabetes of the Young (Chromosome 12), Holt-Oram Syndrome, Angelman Syndrome, Juvenile Glaucoma, Stargardt's Disease, Multiple Endocrine Neoplasia Type 1, Niemann-Pick Disease Type C, Alagille Syndrome, Familial Mediterranean Fever, Tuberous Sclerosis 1, Dystonia, Spinocerebellar Ataxia Type 7, Optz Syndrome, Situs Inversus, Deafness (DFNA1), Pendred Syndrome, and APECED (Inherited Autoimmunity)

Infectious diseases include acquired immunodeficiency syndrome (AIDS) while other diseases comprise, but are not limited to, coronary artery disease, amyotrophic lateral sclerosis (ALS) and rheumatoid arthritis.

Route of administration of the non-replicative retrovirus particles to the patient can be performed by bone implant, bone marrow transplantation, intravenous, intraarterial, intraarticular, intrabronchial, intracoronary, intracranial, sublingual, intradermal, intramuscular, subcutaneous, intrahepatic, intramyocardial, intranasal, intrabronchial, intrathecal, intraprostatic, intraperitoneal, intrapleural, intravesical, intratumoral, intraulcer or transdermal administration. The source of target cell for the gene therapy can be autologous, allogeneic, syngeneic or xenogeneic cells.

The packaging cells of the present invention can also be used to produce non-replicative retroviruses for any other purposes. These purposes include, but are not limited to, gene marking to assess the feasibility of human somatic transgenesis, the fate of a bone marrow autograft in cancer patients, the fate of bone marrow and peripheral blood cell autografts, and the risk of reimplanting malignant cells.

In another embodiment, there is provided the use of a packaging cell line as defined hereinabove to produce a recombinant retrovirus for use in gene therapy.

In a further embodiment, there is provided the use of a retrovirus-packaging cell line for the manufacture of a composition comprising non-replicative retroviral particles for the treatment of diseases treatable with gene therapy.

The present invention will be more readily understood by referring to the following examples which are given to illustrate the invention rather than to limit its scope.

EXAMPLE I

Generation of a High-Titer Packaging Cell Line that can Grow in Suspension and Serum-Free Media Materials and Methods
Construction of the Expression Plasmids All plasmids used to generate GP21C, A2, RD30 and GLV9 clones are derived from the 4.2 kbp pMD2.KG plasmid (derived from pMD.G; Dull T. et al., J. Virol. 1998 November; 72(11):8463-8471) (FIGS. 1A, 1B, 1D & 1E). This vector contains a CMVi.e. promoter followed by a human β-globin intron and a polylinker. Bicistronic vectors derived from pMD2.KG containing an encephalomyocarditis virus (EMCV) IRES followed by a selection gene were used to express gag-pol and env viral proteins. For the purpose of the present invention, a gene encoding for a resistance to either Zeocin™ or puromycin was chosen (zeo$^r$ or puro$^r$). Zeocin™ is the commercial name of a special formulation containing Phleomycin D1, a copper-chelated glycopeptide antibiotic isolated from culture broth of a *Streptomyces verticillus* mutant. The zeo$^r$ gene encodes a small protein named Sh ble that confers drug resistance to bacteria and mammalian cells. Puromycin is an aminonucleoside antibiotic produced by *Streptomyces alboninger* that inhibits peptidyl transfer in eukaryotic, as well as prokaryotic cells. The puro$^r$ gene encodes a puromycin N-acetyl-transferase (PAC) that confers resistance to mammalian cells. pMD2iZeo$^r$ and pMD2iPuro$^r$ were constructed by cloning a 0.9 kbp PstI/XbaI IRES-Zeo$^r$ cassette and a 1.2 kbp IRES-Puro$^r$ cassette in pMD2.KG digested with PstI/NheI.

The plasmid used to generate the GP21C clone was constructed by cloning a 5.2 kbp NotI/NsiI gag-pol insert (from pVPack-GP, Stratagene, La Jolla, Calif.) in pMD2iZeo$^r$ digested by NotI/PstI, to give PMD2GPiZeo$^r$ (FIG. 1A).

The plasmid used to generate the A2 clone was produced from generating pMD2AiPuro$^r$ by ligation of the 1.9 kbp amphotropic env (4070A; pVPack-A, Stratagene; Ott, D. et al., J. Virol. 64 (2), 757-766 (1990)) in pMD2iPuro$^r$ opened with NotI/PstI (FIG. 1B).

The plasmid used to generate the GLV9 clone (FIG. 1D) was produced by amplifying the 2.1 kbp gibbon ape leukemia env (GLV; Delassus et al., Virology. 1989 November; 173(1): 205-213) by the technique of PCR from the genomic DNA of PG13 cells with the forward primer 5'-gtagaattcgatggtattgct-gcct-3' (SEQ ID NO: 1) and the reverse primer 5'-ccgctcgagt-taaaggttaccttcgttc-3' (SEQ ID NO: 2) (EcoRI and XhoI sites are in bold). The GLV env was cloned in pBluescript and sequenced. Then the GLV env was cloned in pMD2iPuro$^r$ digested in EcoRI/XhoI to give pMD2GLViPuro$^r$ (FIG. 1D).

The plasmid used to generate the RD30 clone was produced by amplifying the 1.7 kbp RD114 env (SEQ ID NO. 5) by the technique of PCR from SC3C (a RD114 infectious virus clone) with the forward primer 5'-ccgctcgagatgaaactc-ccaaca-3' (SEQ ID NO: 3) and the reverse primer 5'-cggaat-tctcaatcctgagctt-3' (SEQ ID NO: 4) (XhoI and EcoRI sites are in bold). The RD114 env sequence (SEQ ID NO: 5) had few modifications versus the one found in the nucleotide database (accession X87829). Then the RD114 env was digested in XhoI/XbaI and cloned in pMD2iPuro$^r$ opened with XhoI/XbaI to give pMD2RD114iPuro$^r$ (FIG. 1E).

Cell Culture and Stable Transfection of Expression Plasmids in 293SF Cells, HT-1080 Cells and TE671 Cells.

HT1080 (ATCC CCL-121), TE671 (ATCC CRL-8805), 3T3 (ATCC CRL-1658), 293SF and derivatives cells were cultured in Dulbecco's modified Eagle's medium (DMEM; Sigma, St-Louis, Mo.). These cell lines were maintained in medium supplemented with 10% fetal calf serum (FCS; Bio Cell, Drummondville, Canada). 293SF and derivative cells were also cultured with NCS (Bio Cell). Jurkat and DG75 cell lines were cultured with RPMI supplemented with FCS.

293GP-A2/GFP cells were also cultured in suspension and SFM. The SFM was a low calcium-SFM derived from H-SFM (Invitrogen, Grand Island, N.Y.), and was supplemented with 0.1% (v/v) lipid mixture (Sigma), 0.1% (v/v) BSA (98% purity; Sigma), 0.1% Pluronic F-68 (Sigma) (Cote J. et al., Serum-free production of recombinant proteins and adenoviral vectors by 293SF-3F6 cells. *Biotechnol Bioeng* 1998; 59: 567-575). Cells were routinely cultured in 125 mL shake flasks (Corning, Acton, Mass.) at a concentration varying from $3\times10^5$ up to $1\times10^6$ cells/mL in a 20 mL final volume. They were kept in suspension at a stirrer speed of 120 rpm, 37° C., 100% humidity and 5% $CO_2$ (FORMA Scientific incubator, Marietta, Ohio) on a Big Bill orbital shaker (Barnstead/Thermolyne, Dubuque, Iowa).

Transfection

Figure 2:
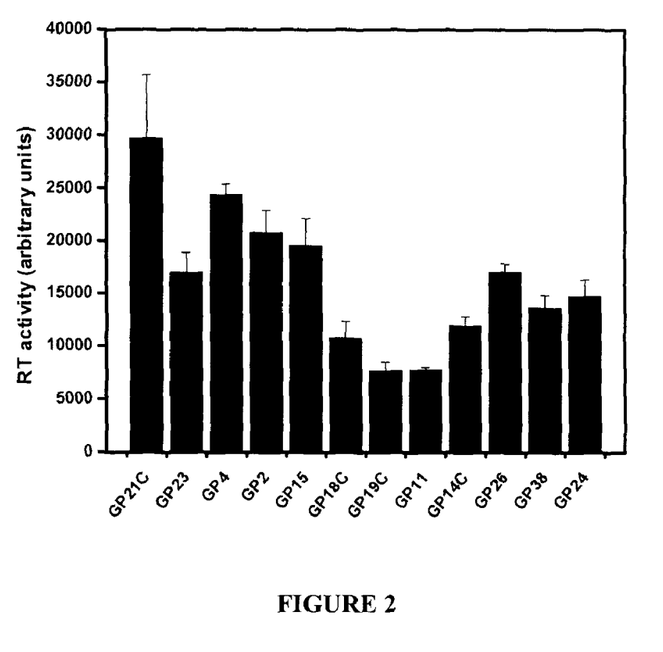
FIG. 2 shows reverse transcriptase activity measured from 12 individual gag-pol expressing clones. Values presented are the mean±standard deviation of an experiment done in triplicate.

Gag-pol clones were generated by transfection using the calcium phosphate procedure. Subconfluent 293SF cells plated in a 10-cm petri-dish were transfected with 10 μg of the pMD2.GPiZeo$^r$ plasmid. Twenty-four hours after transfection, cells were selected in media supplemented with zeocin (400 μg/mL) for two weeks. Zeocin-resistant cells were then subsequently cloned by limiting dilution into 96-well plates and screened using a RT assay (FIG. 2).

The gag-pol clone with the highest level of RT (GP21C) was transfected by calcium phosphate with 10 μg of the pMD2.AiPuro$^r$ plasmid, and cells were selected for two weeks with 0.2 μg/mL of puromycin. The screening of 293GP-A isolated clones was performed by transient transfection. Subconfluent clones grown in 60-mm dishes were individually transfected by the calcium phosphate procedure with 5 μg of the GFP3 transfer vector (FIG. 1C; Qiao J. et al., High translation efficiency is mediated by the encephalomyocarditis virus IRES if the natural sequence surrounding the 11$^{th}$ AUG is retained. *Hum. Gene Ther.* 2002; 13: 881-887), and 5 μg of DNA carrier. Two days later, 1 mL of supernatant of each transfected clone was harvested and used to infect HT1080 cells.

Infection and Transduction

Figure 3:
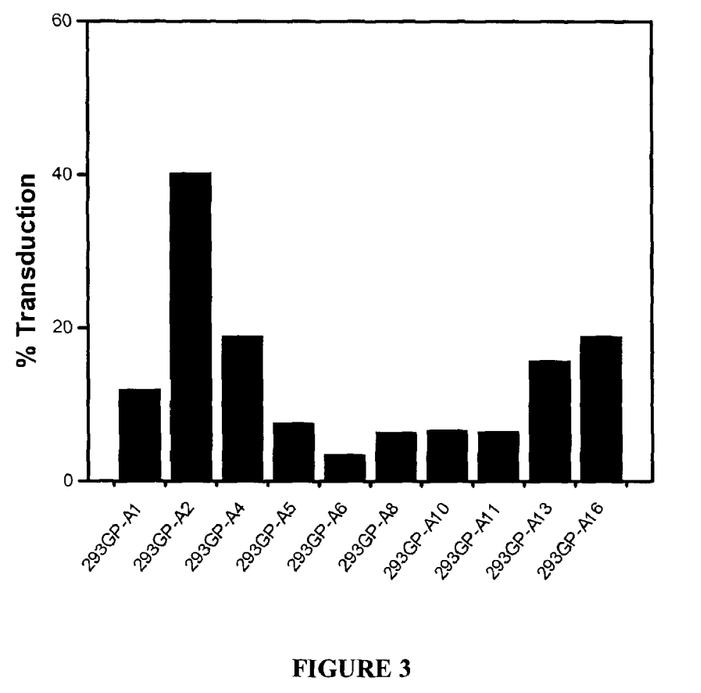
FIG. 3 illustrates the screening of 293GP-A clones for viral production. One mL of supernatant of each transfected clone was harvested and used to infect HT1080 cells. Two days later, target cells were analysed for GFP fluorescence by FACS analysis. Values presented are the mean of duplicate experiments of the 10 best clones.

Virus produced by transient transfection of 293GP-A clones was used to infect 4-5×10$^5$ HT1080 cells in the presence of 8 μg/mL polybrene. Cells were then analysed for GFP fluorescence 2 days after infection by FACS analysis (FIG. 3). The 293GP-A2 clone was selected as the packaging cell line candidate after this screening.

293GP-A2/GFP cells were generated by infection of the 293GP-A2 clone with recombinant GFP retroviruses. GFP viruses were produced by transient transfections and were VSV-G-pseudotyped. Infected cells were then sorted by FACS for GFP fluorescence.

Virus titers were determined by scoring GFP positive target cells by FACS analysis. Briefly, TE671 cells were inoculated at a density of 4.5×10$^5$ cells per well in 6-well plates and cultured in 2 mL of medium overnight. The medium from each well was replaced with 1 mL of serial dilutions of virus supernatants in a 2 mL final volume containing 8 μg/mL polybrene. Forty-eight hours later, cells were trypsinized and analyzed for GFP fluorescence by FACS. Vector titers were calculated as follows: titer=(F×$C_{inf}$/V)×D, where F is the percentage of GFP positive cells, determined by flow cytometry; $C_{inf}$ is the total number of target cells at the time of infection; V is the viral volume applied; and D is the virus dilution factor. Infections resulting in 2-20% of GFP positive cells were considered for titer calculation based on the linear range of the assay. For the transduction assays, adherent cells were plated one day prior infection at 10$^5$ cells/well in a 6-well plate. Twenty-four hours later cells were infected with 0.5 mL of virus in 2 mL final volume containing 8 μg/mL polybrene. Lymphoid cell lines were resuspended at 10$^5$ cells/well in a 12-well plate, and incubated with 250 μl of virus in 1 mL final volume containing 8 μg/mL polybrene. GFP fluorescence was analyzed 2 days after infection.

Reverse Transcriptase Assays (FIG. 2)

The presence of RT in the supernatant of gag-pol clones was measured as follows: 5 μl of supernatant was added to 25 μl of a RT master mix containing 20 μCi/mL dTT32P, 50 mM Tris-HCl, 75 mM KCl, 2 mM DTT, 1 mM MnCl$_2$, 5 μg/mL poly(rA)+oligo dT and 0.5% (v/v) NP-40. The reactions were incubated 4 hours at 37° C. in a 96-well plate, and 6 μl of the total volume was spotted on a DE81 filter paper. The filter was then washed 5 times with 1×SSC for 5 minutes and twice with 85% ethanol for five minutes. The radioactivity associated to the filter was then revealed and quantified with a phosphorimager.

Replication Competent Retrovirus (RCR) Assay

The RCR assay consisted of the mobilization of a GFP vector. 3T3 cells containing a GFP vector were plated at a density of 3×10$^5$ cells per well in 6-well plates. The following day, cells were infected with 2.5 mL of virus produced from the 293GP-A2/GFP cell line cultured in suspension and SFM (10$^8$ IVP). As a positive control, 3T3/GFP cells were also infected with serial dilutions of supernatant produced from 3T3 cells chronically infected by a replication-competent ecotropic MLV. Virus was then allowed to replicate on 3T3/GFP cells for 2 weeks. Supernatants were then harvested and used to infect 3T3 cells. RCR was then evaluated by the presence of GFP cells. GFP cells were observed at up to the 10$^{-8}$ dilution of the positive control.

Screening of Cell Lines Producing High Titers of Recombinant Viruses Pseudotyped with 4070A, GLV, and RD114 env Genes Subconfluent 60-mm dish cellular GP21C clones expressing the different env genes were individually transfected by the calcium phosphate procedure with 5 μg of GFP3, a GFP expressing retroviral plasmid, and 5 μg of DNA carrier. Two days later, 1 ml of supernatant of each transfected clone was harvested and used to infect 4-5×10$^5$ HT-1080 cells in the presence of 8 μg/ml polybrene. The target cells were then analyzed for GFP fluorescence 2 days after infection by FACS analysis.

The generation of stable producer cells expressing GFP recombinant retroviruses was done by using recombinant GFP retroviruses pseudotyped with VSV-G env and produced by transient transfections to infect A2, GLV9 and RD30 clones. Cells were then sorted for GFP fluorescence until more than 95% of the cells became GFP+.

Figure 4:
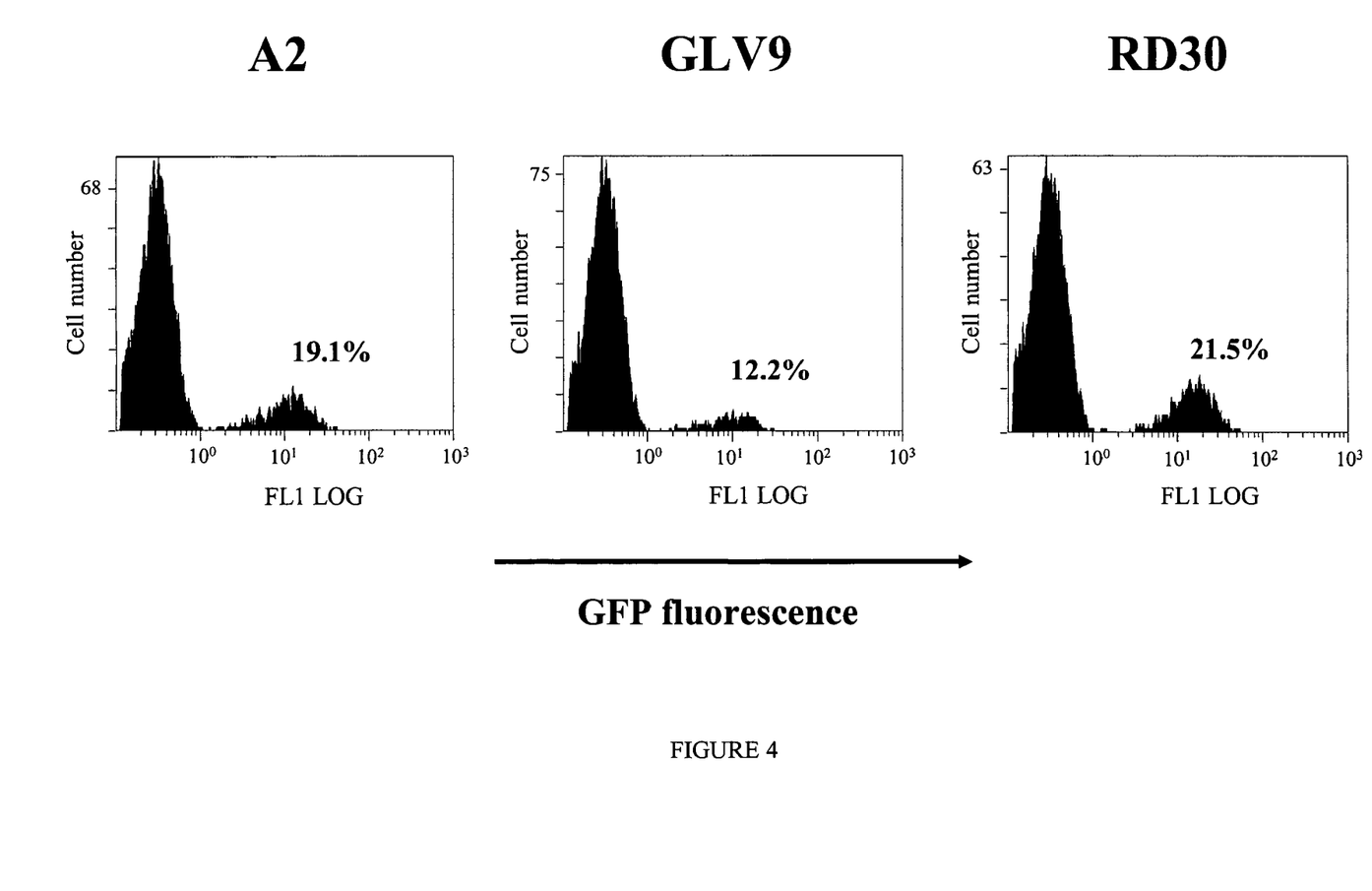
FIG. 4 illustrates the fluorescence intensity from TE671 cells infected with 10 µl of GFP3 virus produced from A2, GLV9 and RD30 clones. The titers calculated were $10^7$ GFP-transducing unit/ml for the virus produced with the A2 cell line, $6\times10^6$ GFP-transducing unit/ml for the virus produced with the GLV9 cell line and $10^7$ GFP-transducing unit/ml for the virus produced with the RD30 cell line.

Viral infectivity was also evaluated on TE671 cells. Briefly, TE671 cells were seeded at 4.5×10$^5$ cells/well in a 6-well plate, and they were infected the next day with 10 μl of viral supernatant harvested from confluent retrovirus producer cells. The infection was performed with 8 μg/ml PB in a 2 ml final volume. Forty-eight hours later, cells were trypsinized and analyzed for GFP fluorescence by FACS (FIG. 4).

Results

Construction of a High-Titer 293SF-Derived Retroviral Packaging Cell Line

Figure 1:
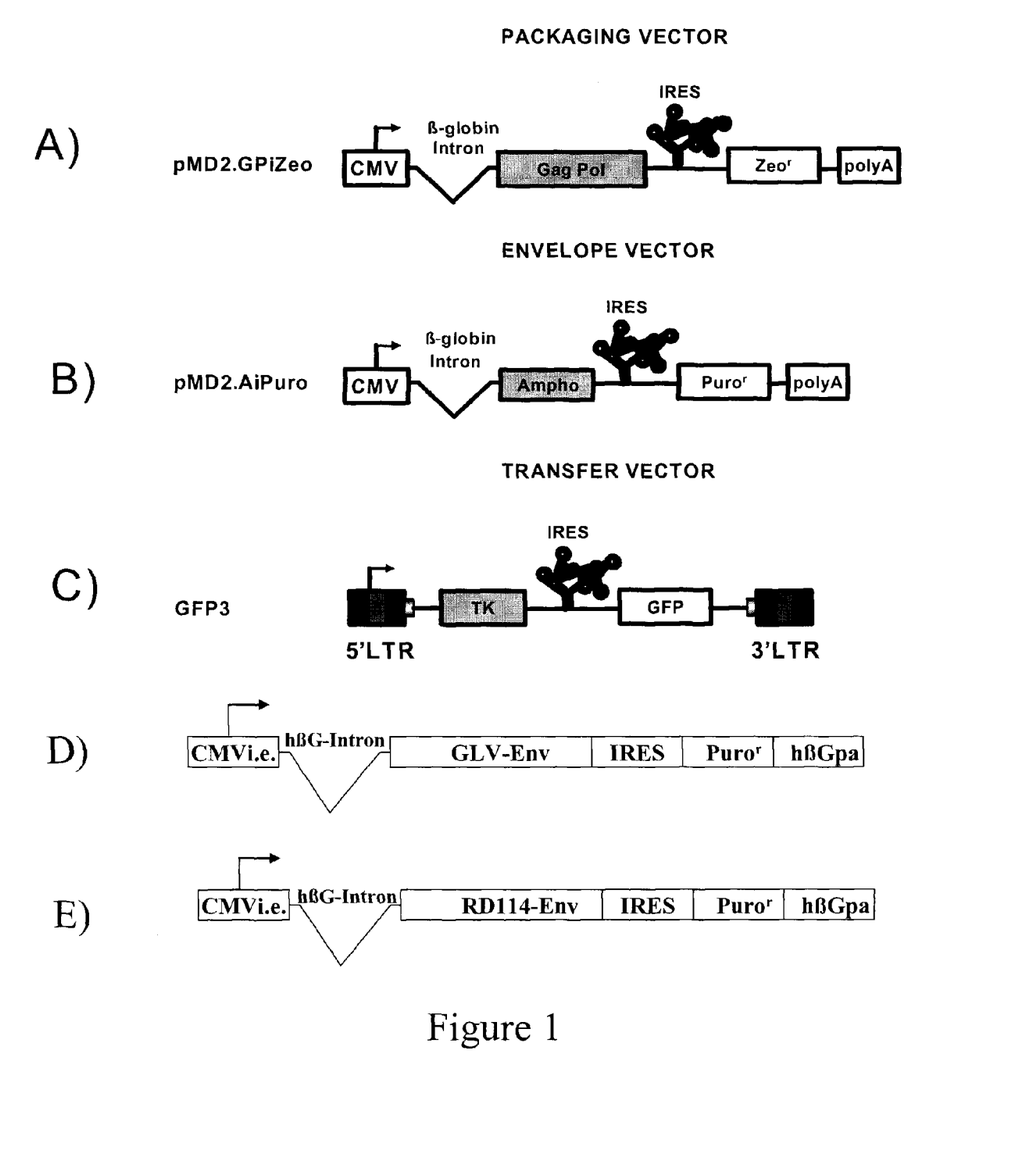
FIG. 1 shows diagrams illustrating the plasmids and retroviral construct: (A) pMD2.GPiZeo and (B) pMD2.AiPuro plasmids contains MLV gag-pol and amphotropic env, respectively, zeocin and puromycin resistance genes are linked to an EMCV IRES sequence; (C) GFP3 is a retroviral vector derived from MLV that contains the herpes simplex thymidine kinase (TK) gene followed by an IRES green fluorescent protein (GFP) sequence; (D) pMD2.GLViPuro and (E) pMD2.RDiPuro clones are of similar construction as B) but with GLV-env and RD-114 env genes respectively. Arrows indicate the start site and the direction of transcription.

MLV gag-pol and envelope (env) genes containing the minimum viral sequence (from ATG to stop codon) were cloned in expression vectors under the control of the cytomegalovirus immediate early enhancer/promoter region (CM-Vi.e.) followed by a β-globin intron. Both plasmids are bicistronic; they contain a viral gene followed by an internal ribosomal entry site (IRES) that allows the expression of a selection marker in a cap-independent manner (FIG. 1).

The packaging vector that expresses gag-pol was stably transfected into 293SF cells, and 12 zeocin-resistant clones were isolated and screened for the presence of reverse transcriptase (RT) in the medium. All clones tested had a RT level ranging from 7000 to 30 000 arbitrary units (FIG. 2). The GP21C clone had the highest level of RT; it was comparable to the one found with the FLYRD18 packaging cell line, and was 15 times higher than the one obtained with PG13 cells (data not shown). Although, a high level of gag-pol expression was achieved with GP21C cells, the cellular growth of this clone and 293SF parental cells was comparable. These data demonstrate that 293SF cells are capable to release efficiently MLV virus cores.

In a second step, the env expression vector was introduced by transfection into the GP21C clone. Puromycin-resistant clones were isolated and screened for vector production by transient transfection of the GFP3 transfer vector. One mL of viral supernatant from the best clones could infect between 3.6% to 40.3% HT1080 cells (FIG. 3). Viruses released from the 293GP-A2 clone were the most efficient to transduce HT1080 cells. This clone was selected as a candidate packaging cell line to produce MLV core pseudotyped with the amphotropic envelope.

A GFP3 transfer vector was stably introduced in the 293GP-A2 clone by infection with VSV-G-pseudotyped retroviruses to assess its potential as a stable retrovirus producer cell line. Cells were then enriched for GFP fluorescence by cell sorting. A titer of $4 \times 10^7$ IVP/mL was obtained with the viral supernatant harvested from 293GP-A2/GFP cells cultured adherently in presence of serum (data not shown). These results indicate that 293GP-A2/GFP cells release high-titer recombinant retroviruses.

Retroviral Vector Titers from 293GP-A2/GFP Cells Cultured in Suspension and SFM

All the packaging cell line construction steps were performed with cells grown adherently and in presence of serum. We next took on the challenge to produce retroviral vectors from the 293GP-A2 packaging cell line in suspension and SFM. For this purpose, 293GP-A2/GFP cells had to be adapted to SFM culture. Cells were first cultured adherently with SFM+5% newborn calf serum (NCS). After three passages cells were transferred into a shake flask at $1 \times 10^6$ cells/mL and cultured under conditions as described above. Cell aggregation without drop of cell viability was observed within the first days. After a 2-week culture, the serum concentration was slowly decreased over a 1-month period until it was completely removed from SFM. Contrary to the suspension adaptation phase, a "crisis" manifested by a drop in cell viability and/or growth rate was observed during the first passages at low serum concentration. Nevertheless, the culture was able to recover from these crisis events. The complete absence of serum led to smaller size cell aggregates (single cells and/or small aggregates with less than 5 cells) depending on the cell density with an overall viability above 95%.

Figure 5A:
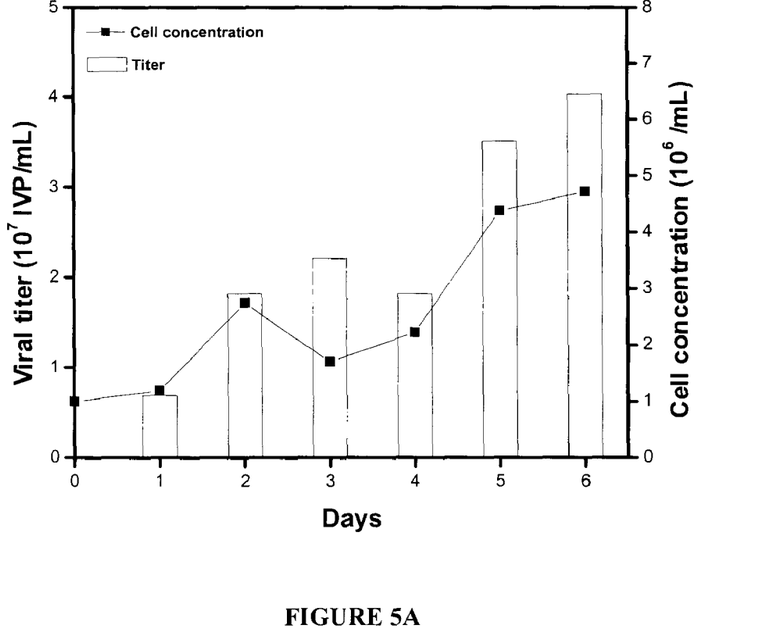
FIG. 5 shows the cellular growth and retroviral vector production from 293GP-A2/GFP cells cultured in suspension in serum-free media (SFM). (A) Cell growth and viral titers were measured each day in a 6-day kinetic period. (B) Viral titers were measured at 3 time points during a 3-month culture period with a cell concentration varying from 4.5 to $5\times10^6$ cells/mL.
Figure 5B:
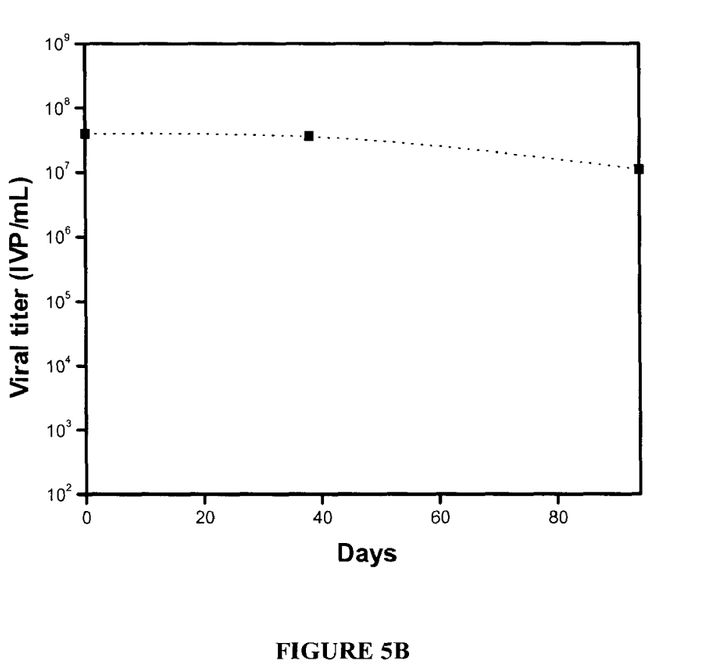

The ability of 293GP-A2/GFP cells to grow and produce vectors in SFM was investigated. 293GP-A2/GFP cells were inoculated in shake flasks at a concentration of $1 \times 10^6$ cells/mL and were submitted to a daily medium replacement. Cellular growth of retrovirus producer cells and viral yields were carefully monitored during a 6-day period. The growth of 293GP-A2/GFP cells reached a maximum cell number of $4.7 \times 10^6$ cells/mL at day 6. Viral titers were superior to $10^7$ IVP/mL from day 2 to day 6 with a maximum level of $4 \times 10^7$ IVP/mL at day 6 (FIG. 5A). Thus, at similar cellular concentrations, titers obtained in suspension with SFM were identical to those obtained with cells cultured adherently in presence of serum ($4 \times 10^7$ IVP/mL). Despite stringent culture conditions (suspension without serum, and without puromycin or zeocin), the retroviral packaging cell line proved to be stable since viral titers were above $10^7$ IVP/mL during a 3-month culture period (FIG. 5B).

Optimal culture conditions of 293GP-A2/GFP cells were determined by testing the impact of cell density and harvest time on vector production. Viral supernatants were collected at 3 different cell densities and at 8 h, 12 h and 24 h time points. The maximum viral titer was achieved at $6 \times 10^6$ cells/mL at all time points, with an average value of $3.6 \times 10^7$ IVP/mL. The increase in cell concentration from $1 \times 10^6$ cells/mL to $3 \times 10^6$ cells/mL led to a parallel 3-fold increase in viral titer. In contrast, increasing the concentration from $3 \times 10^6$ cells/mL to $6 \times 10^6$ cells/mL led only to a 1.4-fold increase in viral titer. Similar titers were obtained at the 3 collection times for each cell density. Titer values at 8 h and 12 h were identical to those obtained at 24 h indicating that an 8-h viral harvest would lead to an optimal viral yield (Table 1).

TABLE 1

Influence of harvest time and cell density on vector production
Titer ($10^7$ IVP/mL)

| Harvest time (h) | $1 \times 10^6$ cells/mL | $3 \times 10^6$ cells/mL | $6 \times 10^6$ cells/mL |
|---|---|---|---|
| 8 | 0.6 ± 0.02 | 2.7 ± 0.05 | 3.6 ± 0.03 |
| 12 | 0.6 ± 0.02 | 2.9 ± 0.12 | 3.5 ± 0.10 |
| 24 | 1.2 ± 0.03 | 2.1 ± 0.05 | 3.6 ± 0.07 |

293GP-A2/GFP cells were inoculated at $6 \times 10^5$ cells/mL in 20 mL of LC-SFM using 125 mL shake flasks. When the cell density reached $1 \times 10^6$ cells/mL, virus production was performed in 3 different shake flasks during an 8, 12 and 24 h period of time. The same culture was then used to reach a cell density of $3 \times 10^6$ and $6 \times 10^6$ cells/mL. A similar virus production protocol was also performed at these two cell concentrations. Values presented are the means ± standard deviation of three independent experiments.

Although the 293GP-A2 packaging cell line was constructed with plasmids that do not contain overlapping retroviral sequences, the absence of RCR in 293GP-A2/GFP cells was confirmed using the RCR assay.

Figure 6:
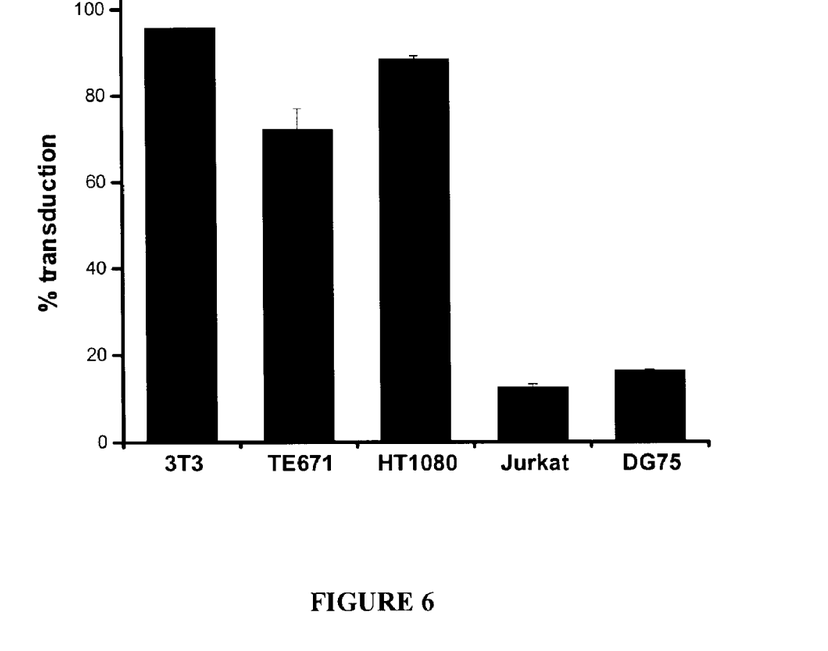
FIG. 6 shows the efficiency of transduction of different cells with virus produced from the 293GP-A2/GFP packaging cell line cultured in suspension and serum-free media (SFM). The transduction efficiency is measured by the percentage of GFP fluorescent cells. Values presented are the mean±standard deviation of triplicate experiments.

Transduction Efficiency of Retroviral Vectors Produced from the 293GP-A2/GFP Producer Cell Line It has been reported that inhibitors of transduction can be released by retroviral packaging cell lines. Therefore, the transduction efficacy of retroviral supernatants produced by 293GP-A2/GFP cells grown in suspension with SFM was tested on 3 adherent and 2 lymphoid cell lines. The 3 adherent cell lines were highly transducible: mouse 3T3 cells were transduced at 95.7%, and human HT1080 and TE671 cells were infected at 88.3% and 72.2%, respectively. DG75 (B lymphoid) and Jurkat (T lymphoid) cell lines were, as expected for suspension cells, less infectable with 16.3% and 12.6% transduction efficiency, respectively, (FIG. 6). These results show that viruses produced in suspension and SFM from 293GP-A2/GFP cells can transduce target cells efficiently.

Discussion

The development of a packaging cell line that grows in suspension and SFM is important for the implementation of late phase clinical trials. In this study, we report the construction of a retroviral packaging cell line derived from 293SF cells. 293GP-A2/GFP cells could produce retroviral vectors at titers up to $4 \times 10^7$ IVP/mL in suspension and SFM.

Gag-pol and env plasmids used to generate the 293GP-A2 packaging cell line contained an IRES followed by a selection marker. Bicistronic vectors were used to prevent the loss of viral proteins that were expressed at high-levels in 293GP-A2 packaging cells. The retroviral packaging cell line proved to be stable which was most likely conferred by the bicistronic vectors used to express viral proteins.

At similar cellular concentrations, titers obtained in suspension with SFM were identical to those obtained with cells cultured adherently in presence of serum ($4 \times 10^7$ IVP/mL). Furthermore, viral titers from 293GP-A2/GFP cells were equivalent or superior to those obtained with other adherent packaging cell lines. It is also important to mention that the 293GP-A2/GFP retroviral producer cell line is a bulk population for the GFP3 vector, and cell cloning has the potential to further increase the titer.

Gag-pol and env expression plasmids used for the generation of 293GP-A2 cells contain the minimum viral sequence to reduce the risk of generating RCR. Using a standard helper assay, no RCR were detected in viral preparations from 293GP-A2/GFP cells (data not shown).

Titers obtained from 293GP-A2/GFP cells cultured in suspension and SFM were in the range of $10^7$ IVP/mL and equivalent after an 8-h, a 12-h and a 24-h production time (Table 1). These data are in agreement with other studies and reflect the half-life at 37° C. of viral particles that ranges between 4 to 8 h. At low cell density, titers increased proportionally to cell concentration, although at higher cell concentrations, from $3 \times 10^6$ to $6 \times 10^6$ cells/mL only a 1.4-fold increase in viral titer was observed. These results suggest that culture conditions at a high cell concentration could be limiting in SFM. Optimization procedures will be tested in the future to increase viral productivity. For example, large-scale vector production with 293GP-A2/GFP cells will be optimized in bioreactors with a perfusion system as we have previously reported in short term cultures of 293GPG cells (Ghani K et al. Retroviral vector production using suspension-adapted 293GPG cells in a 3 L acoustic filter-based perfusion bioreactor. *Biotechnol Bioeng* 2006; 95: 653-660). The continuous feeding of cells and vector harvest should increase cell growth and viral productivity. Many clinical gene therapy studies are showing efficacy, and the use of bioreactors with cells cultured in suspension and SFM could be the ideal set-up for large-scale vector production needed for patient treatments.

Vectors produced from 293GP-A2/GFP cells were able to transduce efficiently adherent cells, but the percentage was not as high with suspension target cells (FIG. 6). This transduction difference can be explained by a lower adsorption ability of retroviral vectors to lymphoid cellular membranes.

Recombinant retroviruses can incorporate heterologous envelope glycoproteins at their surface. This process known as pseudotyping is used to increase viral infectivity and modify vector tropism. New packaging cell lines could be derived from the GP21C clone to produce viruses pseudotyped with the cat RD114 env or the Gibon ape leukemia env. These vectors produced in suspension and SFM could be useful for ex vivo gene therapy approaches that target hematopoietic cells.

Figure 7:
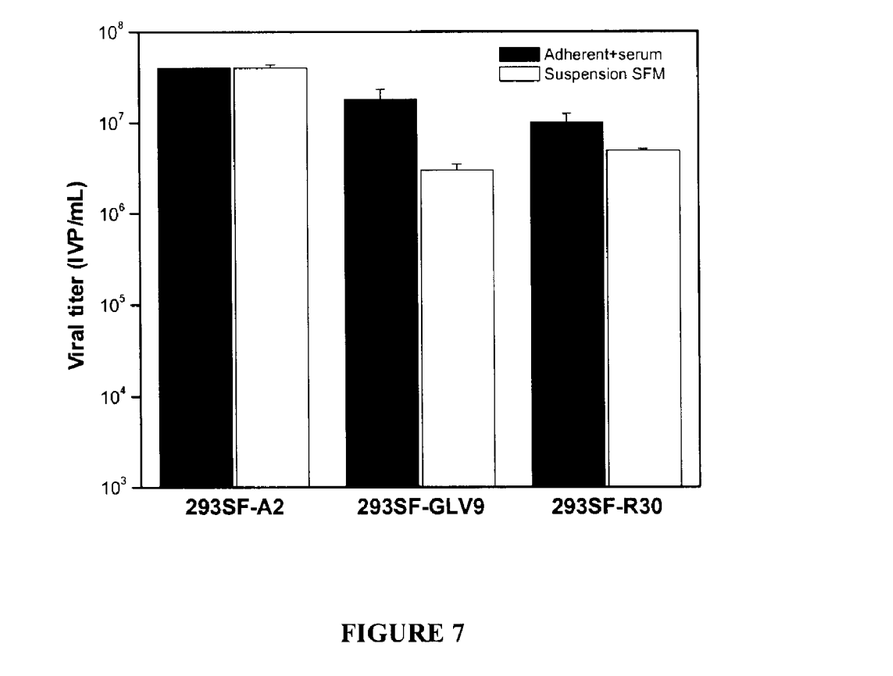
FIG. 7 shows a comparative graph of viral titers with GFP3 virus obtained from different packaging cell lines grown in adherent conditions in medium with serum and also grown in suspension in serum-free medium.

In conclusion, this invention provides for the first time the engineering of a packaging cell lines that produce high-titer retroviral vectors in suspension and serum-free media (FIG. 7). The 293GP-A2, -GLV9 and -RD30 cell lines have the potential for the large-scale biomanufacturing of retroviral vectors, and it should be ideal for the implementation of late phase cancer gene therapy clinical trials with a high number of patients.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

---

We claim:

1. A retrovirus packaging cell line for the production of a non-replicative retrovirus particle wherein the cell line comprises stably integrated a gag gene, a pol gene and an env gene, wherein said gag gene and said pol gene are from murine Moloney leukemia virus, wherein said env gene is selected from a feline RD114 env gene, a gibbon ape leukemia env gene, and an amphotropic 4070A env gene, and wherein said retrovirus packaging cell line is selected from cell line RD30 deposited under accession number 310106-01, Jan. 31, 2006 from the International Depositary Authority of Canada (IDAC), cell line GLV deposited under IDAC accession number 310306-02, Jan. 31, 2006 and cell line A2 deposited under IDAC accession number 310106-04, Jan. 31, 2006.

* * * * *

SEQUENCE LISTING

```
<160> NUMBER OF SEQ ID NOS: 5

<210> SEQ ID NO 1
<211> LENGTH: 25
<212> TYPE: DNA
<213> ORGANISM: artificial
<220> FEATURE:
<223> OTHER INFORMATION: primer

<400> SEQUENCE: 1
gtagaattcg atggtattgc tgcct                                          25

<210> SEQ ID NO 2
<211> LENGTH: 28
<212> TYPE: DNA
<213> ORGANISM: artificial
<220> FEATURE:
<223> OTHER INFORMATION: primer

<400> SEQUENCE: 2
ccgctcgagt taaaggttac cttcgttc                                       28

<210> SEQ ID NO 3
<211> LENGTH: 24
<212> TYPE: DNA
<213> ORGANISM: artificial
<220> FEATURE:
<223> OTHER INFORMATION: primer

<400> SEQUENCE: 3
ccgctcgaga tgaaactccc aaca                                           24

<210> SEQ ID NO 4
<211> LENGTH: 22
```

```
<212> TYPE: DNA
<213> ORGANISM: artificial
<220> FEATURE:
<223> OTHER INFORMATION: primer

<400> SEQUENCE: 4
cggaattctc aatcctgagc tt                                              22

<210> SEQ ID NO 5
<211> LENGTH: 1698
<212> TYPE: DNA
<213> ORGANISM: Feline leukemia virus

<400> SEQUENCE: 5
atgaaactcc caacaggaat ggtcatttta tgtagcctaa taatagttcg ggcagggttt     60
gacgaccccc gcaaggctat cgcattagta caaaaacaac atggtaaacc atgcgaatgc    120
agcggagggc aggtatccga ggccccaccg aactccatcc aacaggtaac ttgcccaggc    180
aagacggcct acttaatgac caaccaaaaa tggaaatgca gagtcactcc aaaaaatctc    240 accccctagcg ggggagaact ccagaactgc ccctgtaaca ctttccagga ctcgatgcac    300
agttcttgtt atactgaata ccggcaatgc agggcgaata taagacata ctacacggcc     360 accttgctta aaatacggtc tgggagcctc aacgaggtac agatattaca aaaccccaat    420
cagctcctac agtccccttg taggggctct ataaatcagc ccgtttgctg gagtgccaca    480
gcccccatcc atatctccga tggtggagga cccctcgata ctaagagagt gtggacagtc    540
caaaaaaggc tagaacaaat tcataaggct atgcatcctg aacttcaata ccacccctta    600
gccctgccca agtcagaga tgaccttagc cttgatgcac ggacttttga tatcctgaat    660 accacttttta ggttactcca gatgtccaat tttagccttg cccaagattg ttggctctgt    720
ttaaaactag gtaccccctac ccctcttgcg atacccactc cctctttaac ctactcccta    780
gcagactccc tagcgaatgc ctcctgtcag attatacctc ccctcttggt tcaaccgatg    840
cagttctcca actcgtcctg tttatcttcc cctttcatta acgatacgga acaaatagac    900
ttaggtgcag tcaccttttac taactgcacc tctgtagcca atgtcagtag tccttattgt    960
gccctaaacg ggtcagtctt cctctgtgga ataacatgg catacaccta tttaccccca   1020
aactggacag actttgcgt ccaagcctcc ctcctcccg acattgacat catcccgggg   1080
gatgagccag tccccattcc tgccattgat cattatatac atagacctaa acgagctgta   1140
cagttcatcc ctttactagc tggactggga atcaccgcag cattcaccac cggagctaca   1200
ggcctaggtg tctccgtcac ccagtataca aaattatccc atcagttaat atctgatgtc   1260
caagtcttat ccggtaccat acaagattta caagaccagg tagactcgtt agctgaagta   1320
gttctccaaa ataggagggg actggaccta ctaacggcag aacaaggagg aatttgttta   1380
gccttacaag aaaatgctg ttttttatgct aacagtcag gaattgtgag aaacaaaata   1440
agaaccctac aagaagaatt acaaaaacgc agggaaagcc tggcatccaa ccctctctgg   1500
accgggctgc agggctttct tccgtacctc ctacctctcc tgggacccct actcaccctc   1560
ctactcatac taaccattgg gccatgcgtt ttcagtcgcc tcatggcctt cattaatgat   1620
agacttaatg ttgtacatgc catggtgctg gcccagcaat accaagcact caaagctgag   1680
gaagaagctc aggattga                                                 1698
```